United States Patent [19]

Andersson et al.

[11] Patent Number: 5,144,948
[45] Date of Patent: Sep. 8, 1992

[54] APPARATUS FOR STIMULATING LIVING TISSUE WITH MEANS TO CONTROL STIMULATING PULSE TIME INTERVAL

[75] Inventors: Peter Andersson, Stockholm; Bo Koepsen, Balsta; Jonas Berglin, Alvsjo; Josef Vock, Spanga, all of Sweden

[73] Assignee: Siemens Aktiengesellschaft, Munich, Fed. Rep. of Germany

[21] Appl. No.: 711,863

[22] Filed: Jun. 7, 1991

[30] Foreign Application Priority Data

Jun. 15, 1990 [SE] Sweden ................................ 9002129

[51] Int. Cl.$^5$ ............................................... A61N 1/36
[52] U.S. Cl. .................................................. 128/419 PG
[58] Field of Search .................. 128/419 PG, 419 PS, 128/419 PT

[56] References Cited

U.S. PATENT DOCUMENTS

| 3,757,792 | 9/1973 | Mulier et al. ...................... | 128/419 P |
| 4,074,720 | 2/1978 | Malchman et al. ........... | 128/419 PG |
| 4,091,817 | 5/1978 | Thaler ............................ | 128/419 PG |
| 4,290,429 | 9/1981 | Blaser ............................ | 128/419 PT |
| 4,463,769 | 8/1984 | Elmqvist ....................... | 128/419 PG |
| 4,606,350 | 8/1986 | Frost .............................. | 128/419 PG |
| 4,686,990 | 8/1987 | Moberg ......................... | 128/419 PT |
| 4,715,381 | 12/1987 | Moberg ......................... | 128/419 PT |

FOREIGN PATENT DOCUMENTS 0269846 10/1987 European Pat. Off. .
0249821 12/1987 European Pat. Off. ...... 128/419 PG Primary Examiner—William E. Kamm
Assistant Examiner—J. R. Jastrzab
Attorney, Agent, or Firm—Hill, Van Santen, Steadman & Simpson

[57] ABSTRACT

An apparatus for stimulating living tissue delivers a stimulating pulse with a predetermined stimulating pulse amplitude and a stimulating pulse duration. Each stimulating pulse is separated by a stimulating pulse time interval, which is controlled by a control device. Maintenance of the predetermined stimulating pulse amplitude is undertaken by continuous control of the stimulating pulse time interval by means of the control device, which increases the value of a predetermined minimum stimulating pulse time interval to a new value if the time period, from the time when the voltage across an output capacitor reaches the value of the stimulating pulse amplitude until the time when the stimulating pulse is delivered, is shorter than a safety time interval established by the control device.

8 Claims, 2 Drawing Sheets

APPARATUS FOR STIMULATING LIVING TISSUE WITH MEANS TO CONTROL STIMULATING PULSE TIME INTERVAL

BACKGROUND OF THE INVENTION

1. Field of the Invention

The present invention is directed to an apparatus for stimulating living tissue, such as an implantable heart pacemaker, including means for insuring that a predetermined amplitude of the stimulating pulse is maintained over time.

2. Description of the Prior Art

An apparatus for stimulating living tissue, in the form of an implantable heart pacemaker, is disclosed in European application 0 071 965, which includes a battery having an internal resistance, which is dependent on the charge of the battery. A stimulating pulse generator is connected to the battery and includes an output capacitor, which is relatively slowly charged by the battery. To deliver a stimulating pulse, the capacitor is quickly discharged across the tissue to be stimulated. A measuring device is provided which measures the voltage across the output capacitor. A control device selects a predetermined value for the stimulating pulse amplitude. The control device controls the stimulating pulse generator so as to enable release of a stimulating pulse dependent on a predetermined stimulating pulse time interval, as well as on whether the voltage across the output capacitor, measured by the measuring device, has reached the predetermined value for the stimulating pulse amplitude.

In this known pacemaker, the stimulating pulses are separated by defined stimulating pulse time intervals. The pacemaker is provided with a battery for charging an output capacitor, which, for delivering a stimulating pulse, is discharged across the heart tissue. The internal resistance of the battery increases with time, which in turn increases the charging time of the output capacitor. In order to guarantee that a stimulation is always carried out with efficient stimulating pulse amplitude, the voltage across the output capacitor is measured and a stimulating pulse is not delivered until a defined minimum voltage has been reached. This means that the stimulating pulse is delayed if the output capacitor is not charged to the minimum voltage at the time when the stimulating pulse should have been delivered according to the defined stimulating pulse time interval. This delay results in a loss of control of the stimulating pulse time interval as it will be the charging time of the output capacitor that will determine the stimulating pulse time interval, and the charging time may vary. In particular, if the stimulating pulse amplitude and/or the stimulating pulse duration varies, the charging time of the output capacitor will vary.

SUMMARY OF THE INVENTION

It is an object of the present invention to provide an apparatus, in which a stimulating pulse amplitude, selected by the control device, is guaranteed and in which the stimulating pulse time interval is controllable by the control device, irrespective of any variations in stimulating pulse amplitude and stimulating pulse duration.

The above object is achieved in accordance with the principles of the present invention in an apparatus for stimulating living tissue having a control device which sets a minimum value of the stimulating pulse time interval and, which increases the minimum value if the time period, from the time when the voltage across the output capacitor has reached the value of the stimulating pulse amplitude until the time when the stimulating pulse is delivered, is shorter than a predetermined safety time interval selected by the control device.

Thus, the delivery of the stimulating pulse with the predetermined stimulating pulse amplitude, selected by the control device and with the controllable stimulating pulse time interval is ensured. Further, the safety time interval gives room for variations in stimulating pulse amplitude, stimulating pulse duration, stimulating pulse time interval and in impedance of the living tissue without any danger of the stimulating pulse being insufficient to stimulate the tissue or of it having an uncontrollable stimulating pulse time interval.

In one embodiment of the apparatus, the time period is measured by a time counter, which is activated by the control device when the voltage across the output capacitor reaches the predetermined value of the stimulating pulse amplitude, selected by the control device, and which is interrupted when the stimulating pulse is delivered. The control device compares the counted value of the time period with the safety time interval. This gives the advantage that the control device can determine the difference between the time period and the safety time interval and, based on the difference, determine whether an increase of the value of the minimum stimulating pulse time interval is necessary, and also determine how large an increase needs to be so that the time period becomes longer than the safety time interval.

In a further embodiment, a time counter is activated by the control device when the voltage across the output capacitor reaches the predetermined value of the stimulating pulse amplitude selected by the control device. The time counter is activated during a time interval corresponding to the safety time interval. The control device detects whether the time counter has interrupted its counting before the stimulating pulse is delivered. The advantage is that the control device only has to decide whether the stimulating pulse has been delivered before the time counter is interrupted, and thereby the apparatus is easier to manufacture.

In another embodiment, the charging time of the output capacitor is measured by a time counter, which is activated by the control device when a stimulating pulse is delivered. The time counter is interrupted when the voltage over the output capacitor reaches the predetermined value of the stimulating pulse amplitude selected by the control device. The control device calculates the time period based on the counted value of the charging time and the stimulating pulse time interval. The control device compares the calculated time period with the safety time interval to establish whether the time period is shorter than the safety time interval. Thus, an immediate control of the change in charging time over a period of time of the output capacitor is achieved, which change is dependent on parameters such as stimulating pulse amplitude and stimulating pulse duration. Further, the difference between the time period and the safety time interval may be determined already before the stimulating pulse is delivered. The value of the minimum stimulating pulse time interval may thereby be increased also during the stimulating pulse time interval, in which the time period is shorter than the safety time interval.

In another embodiment, a detector detects the response from the tissue when a stimulating pulse is delivered and the control device, based on the detected response, selects a stimulating pulse amplitude, which is at a defined safety distance from the lowest stimulating pulse amplitude that causes a response from the tissue. In pacemakers, this is known as autocapture and is described in, for example U.S. Pat. No. 3,757,792. However, in connection with the present invention there are additional advantages, because a pacemaker with a autocapture function sets the stimulating pulse amplitude just above the stimulating threshold of the heart and therefore is more sensitive to changes in stimulating pulse amplitude and stimulating pulse duration when the charging time of the output capacitor is increased. In particular, in modern pacemakers, which can inhibit the delivery of stimulating pulses as long as the patient's heart is beating spontaneously, the changes in stimulating pulse amplitude and stimulating pulse duration may be significant after a period of inhibition.

In all embodiments, the increase of the minimum stimulating pulse time interval may be performed in successive steps until the time period exceeds the safety time interval. This means that a slow adaption to the new conditions is possible to carry out with full control of the stimulating pulse interval.

Alternatively, the increase in the minimum stimulating pulse time interval may be performed in one step, which is selected by the control device and which is long enough to make the time period exceed the safety time interval. In this way, full control of the stimulating pulse time interval is still possible at the same time as, if the increase is specifically selected, the patient's attention can be drawn to the fact that the charge of the battery has decreased to a level where certain functions of the pacemaker are limited and that a visit to a physician may be necessary in order to thoroughly establish the status of the battery.

In this context, it is advantageous to have the value of the minimum stimulating pulse time interval, after its increase to a new value, slowly decreasing toward the preceding value until the time period is equal to the safety time interval. This makes it possible to use the margins that are present due to the fact that the increase is greater than necessary and to the fact that the charging time of the output capacitor may decrease.

In order to make use of the margins more effectively, the control device may suitably vary the value of the safety time interval based on, inter alia, actual stimulating pulse amplitude, actual stimulating pulse duration, resistance of the battery, etc, so that an optimal safety time interval is present at every defined stimulating pulse.

DESCRIPTION OF THE PREFERRED EMBODIMENTS

Figure 1:
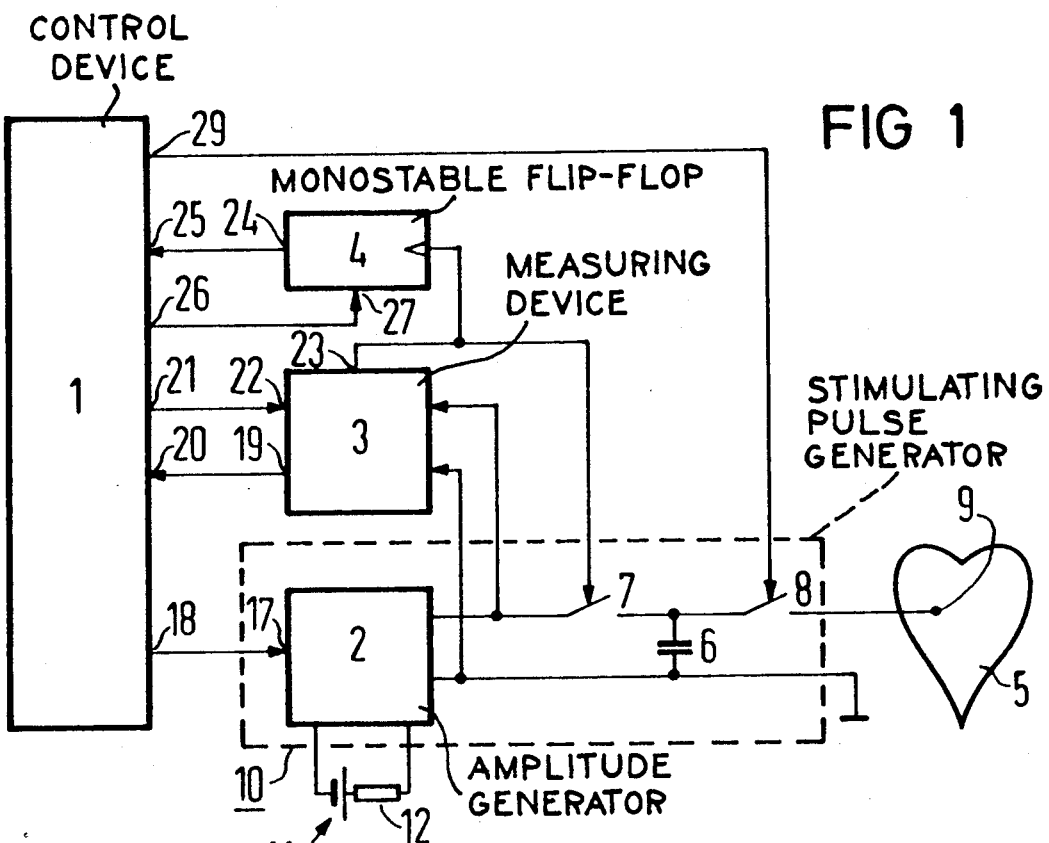
FIG. 1 is a schematic block diagram of an apparatus for stimulating living tissue, in the form of a heart pacemaker, constructed in accordance with the principles of the present invention.

FIG. 1 shows a first embodiment of an apparatus according to the invention in form of a block diagram of a pacemaker. The pacemaker comprises a stimulating pulse generator 10 with an amplitude generator 2, which is connected to a battery 11 having an internal resistance 12, and an output capacitor 6, a control device 1, a measuring device 3 and a monostable flip-flop 4. The amplitude generator 2 has an input 17, which is connected to an output 18 of the control device 1. By means of this connection, the control device 1 can control the charging by the amplitude generator 2 of the output capacitor 6. The output capacitor 6 is charged via a charge output of the amplitude generator 2 when a first switch 7 is closed. When the required voltage across the output capacitor 6 has been reached, the first switch 7 is opened and a stimulating pulse can be delivered if a second switch 8 is closed, whereby the output capacitor 6 is discharged via an electrode tip 9 across a heart 5.

The voltage across the output capacitor 6 is measured continuously during the charging by the measuring device 3, which has a measure input connected to the charge output of the amplitude generator 2. The value of the measured voltage is forwarded from an output 19 of the measuring device 3 to an input 20 of the control device 1. From an output 21, the control device 1 can transfer a selected voltage value, which corresponds to a predetermined stimulating pulse amplitude, to an input 22 of the measuring device 3. The measuring device 3 compares the selected voltage value with the measured voltage across the output capacitor 6, and, when the measured voltage reaches the selected voltage value, a signal from output 23 of the measuring device 3 opens the first switch 7 and simultaneously activates the monostable flip-flop 4. The monostable flip-flop 4 runs through a predetermined safety time interval $T_a$ selected by the control device 1, and then falls back to its original position. Information about the status of the monostable flip-flop 4 is forwarded from a status output 24 of the monostable flip-flop 4 to a status input 25 of the control device 1. The safety time interval $T_a$ can be changed by the control device 1 via an output 26, which leads to an input 27 of the monostable flip-flop 4.

The control device 1 selects a stimulating pulse time interval, and, when a stimulating pulse is to be delivered, a signal from output 29 of the control device 1 closes the second switch 8. The stimulating pulse time interval is limited by a predetermined minimum stimulating pulse time interval, and, as long as the monostable flip-flop 4 falls back to its original position before the second switch 8 is closed by the control device 1, no other measures are necessary.

As the internal resistance 12 of the battery 11 increases with time, the charging time of the output capacitor 6 is increased. Finally, the monostable flip-flop 4 will not be able to fall back before the second switch 8 is closed by the control device 1, and the control device 1 increases the value of the minimum stimulating pulse time interval so there will be enough time for the monostable flip-flop 4 to fall back before the second switch 8 is closed by the control device 1.

Figure 2:
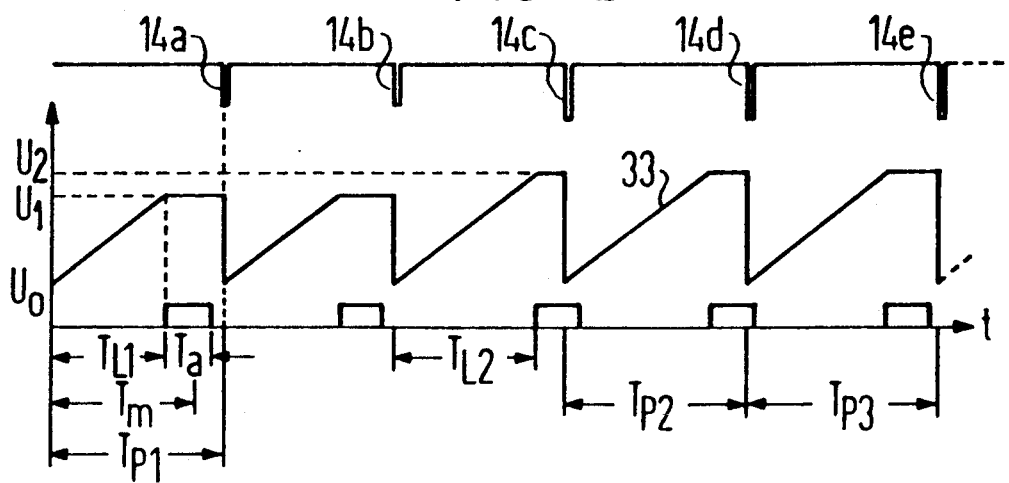
FIGS. 2, 3 and 4 are voltage/time diagrams showing the voltage across the output capacitor correlated with various pulses occurring in the operation of the device shown in FIG. 1.
Figure 3:
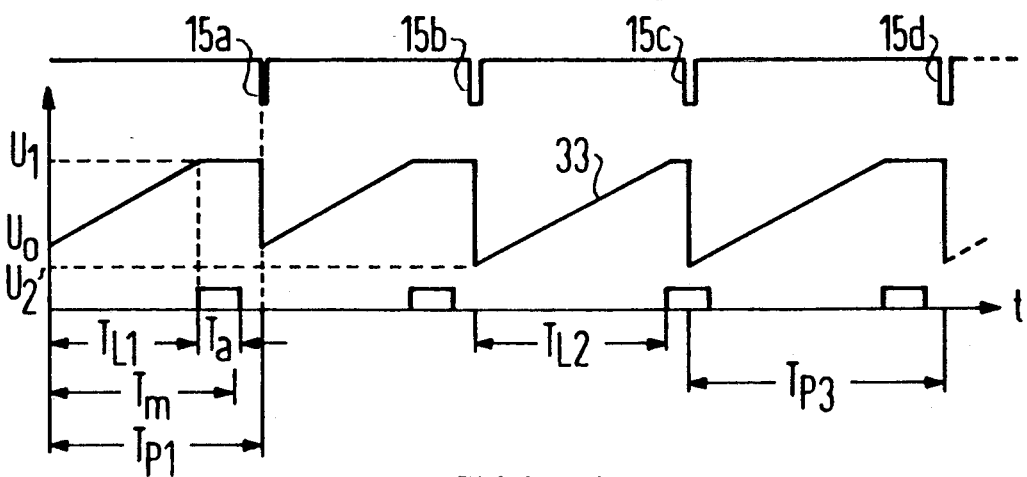
Figure 4:
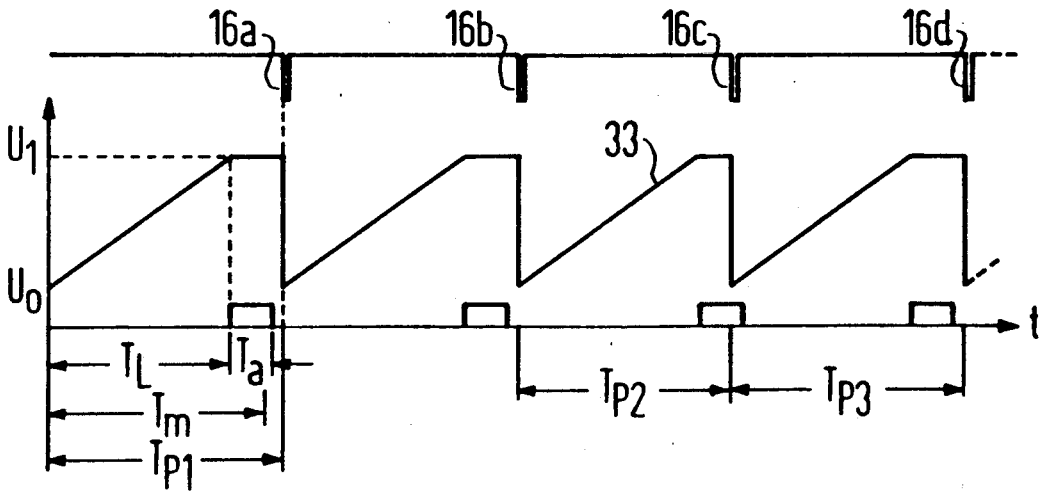

FIGS. 2-4 show how the pacemaker according to FIG. 1 operates in different situations. In order to emphasize the operational principles, some simplifications have been made. For example, the charge characteristic of the output capacitor 6 is illustrated by a straight line, the discharge is illustrated as an instant event and, as illustrated in FIG. 2, the output capacitor 6 is discharged to the same residual voltage at an increased stimulating pulse amplitude as at a lower stimulating pulse amplitude.

The upper part of the diagram in FIG. 2 shows a sequence consisting of five stimulating pulses 14a-14e, where the control device 1, before the third stimulating pulse 14c, has commanded an increase of the stimulating pulse amplitude. In the lower part of the diagram, the load line 33 of the output capacitor 6 is shown during the generation of the stimulating pulses 14a-14e.

The first two stimulating pulse time intervals $T_{P1}$ are identical and the output capacitor 6 is charged from a residual voltage $U_0$ to a voltage $U_1$ which corresponds to the stimulating pulse amplitude. The charging time $T_{L1}$ is short enough to allow the entire safety time interval $T_a$ to expire before the stimulating pulse is delivered. The minimum stimulating pulse time interval $T_m$ is indicated in the diagram. Before the third stimulating pulse 14c, the control device 1 commands an increase of the stimulating pulse amplitude and this causes the output capacitor 6 to be charged to a higher voltage $U_2$. The charging time $T_{L2}$ will be longer than the previous charging time $T_{L1}$ and there is not enough time for the safety time interval $T_a$ to expire within the stimulating pulse time interval $T_{P1}$. Before the fourth stimulating pulse 14d, the control device 1 increases the value of the minimum stimulating pulse time interval $T_m$, which in this case causes the stimulating pulse time interval $T_{P1}$, to be increased to $T_{P2}$. Also the second stimulating pulse time interval $T_{P2}$ is too short to allow the safety time interval $T_a$ to expire before the stimulating pulse 14d is delivered. The value of the minimum stimulating pulse time interval $T_m$ is therefore increased also before the fifth stimulating pulse 14e, and, thereby, the value of the stimulating pulse time interval $T_{P2}$ is increased to $T_{P3}$. As the stimulating pulse time interval $T_{P3}$ is sufficiently long, no further adjustments are necessary. If the control device 1 lowers the voltage $U_2$ back to $U_1$, it is possible to allow the value of the minimum stimulating pulse time interval $T_m$ to slowly decrease again towards its most recent value or towards a value that is determined by the charging time $T_L$ plus the safety time interval $T_a$.

In FIG. 3, another sequence is shown. This sequence consists of four stimulating pulses 15a-15d. The control device 1 has, before the second stimulating pulse 15b, commanded an extension of the stimulating pulse duration. In the first stimulating pulse time interval $T_{P1}$, the output capacitor 6 is charged from a residual voltage $U_0$ to a voltage $U_1$. The charging time $T_{L1}$ is short enough to allow the safety time interval $T_a$ to expire before the stimulating pulse 15a is delivered. Before the second stimulating pulse 15b, the control device 1 has commanded an extended stimulating pulse duration, which is illustrated by a broader stimulating pulse 15b. The extended stimulating pulse 15b causes the voltage to drop to a lower residual voltage $U_2$ when the stimulating pulse 15b is delivered. As a consequence, the charging time $T_{L2}$ of the output capacitor 6 will be longer, before the third stimulating pulse 15c, than the previous charging time $T_{L1}$, and the stimulating pulse 15c is delivered before the safety time interval $T_a$ has expired. Before the fourth stimulating pulse 15d, the control device commands an increase of the value of the minimum stimulating pulse time interval $T_m$, and in this case, the increase is determined by the value of the stimulating pulse time interval $T_{P1}$ and selected long enough so that the new value of the minimum stimulating pulse time interval $T_m$ is significantly higher than $T_{P1}$. The new stimulating pulse time interval $T_{P2}$ is now long enough for both the charging time $T_{L2}$ plus the safety time interval $T_a$ to expire before the stimulating pulse 15d is delivered.

In FIG. 4, a third sequence is shown, which consists of four stimulating pulses 16a-16d. Here, the control device 1 has commanded a shorter stimulating pulse time interval before the third stimulating pulse 16c. The first two stimulating pulse time intervals $T_{P1}$ are identical and, as described earlier, the output capacitor 6 is charged from the residual voltage $U_0$ to a voltage $U_1$. Before the third stimulation pulse 16c, the control device 1 commands a decrease of the value of the stimulating pulse time interval $T_{P1}$ to a new value $T_{P2}$. In this case, the safety time interval $T_a$ does not have time to expire before the stimulating pulse 16c is delivered. The reason for this may, for example, be that the charging time $T_L$ has slowly increased over a period of time, while an increase of the predetermined value of the minimum stimulating pulse time interval $T_m$ has not been necessary. However, before the fourth stimulating pulse 16e, an increase takes place, and a new stimulating pulse time interval $T_{P3}$, which is equal to the new value of the minimum stimulating pulse time interval $T_m$, is obtained. The stimulating pulse time interval $T_{P3}$ does not have to be as long as $T_{P1}$; it is sufficient if it is long enough to accommodate the charging time $T_L$ and the safety time interval $T_a$.

Figure 5:
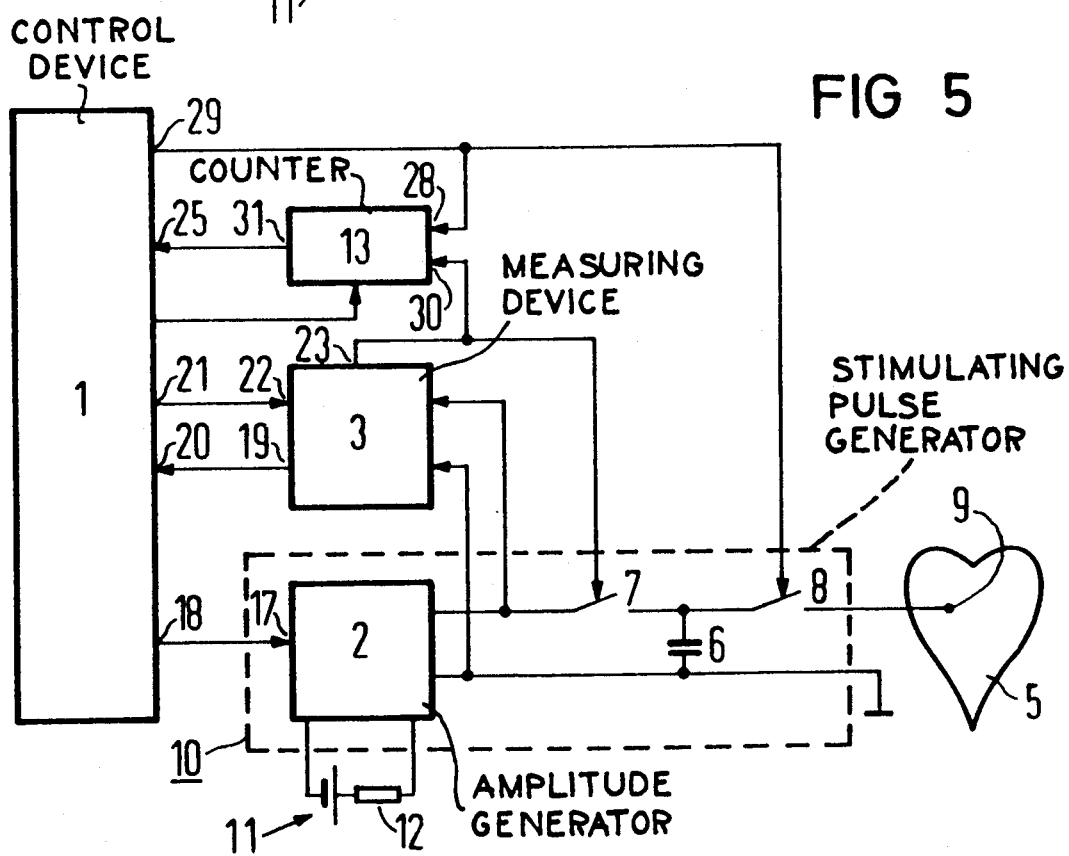
FIG. 5 is a schematic block diagram of a further embodiment of an apparatus for stimulating living tissue, in the form of a heart pacemaker, constructed in accordance with the principles of the present invention.

FIG. 5 shows an alternative block diagram for the pacemaker. The monostable flip-flop 4 in the block diagram in FIG. 1 is here replaced by a time counter 13, which, by means of an input 28, is directly connected to the output 29 of the control device 1 and by means of an input 30 to the output 23 of the measuring device 3. The time counter 13 also has an output 31 which is connected to the input 25 of the control device 1. Otherwise the block diagram in FIG. 5 is identical with the block diagram in FIG. 1. When the output capacitor 6 has been charged to the correct voltage, the measuring device 3 sends a signal that opens the first switch 7 and activates the time counter 13. When the control device 1 sends a signal which closes the second switch 8 and thereby delivers the stimulating pulse, this signal is simultaneously forwarded to the time counter 13, which stops its counting. The time counter 13 sends the counted value to the control device 1, which compares the value with the safety time interval $T_a$ to determine whether an increase of the value of the minimum stimulating pulse time interval $T_m$ is necessary.

The pacemaker according to the block diagram in FIG. 5 may also function so that the time counter 13 is activated when the control device 1 sends the signal which closes the second switch 8, and so that the counting stops when the output capacitor 6 has been charged for the upcoming stimulating pulse. The time counter 13 then transfers the counted value to the control device 1, which, based on the measured charging time and the value of the ongoing stimulating pulse time interval, calculates the value of the time period between the time when the output capacitor 6 is charged and the time when the stimulating pulse is delivered. The time period is then compared with the safety time interval $T_a$ to determine whether an increase of the minimum stimulating pulse time interval is necessary.

Although modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for electrically stimulating living tissue comprising:

a battery having an internal resistance which is dependent on the charge of the battery;

a stimulating pulse generator connected to said battery and having an output capacitor, adapted for connection across tissue to be stimulated, which is charged by said battery, said stimulation pulse generator including means for rapidly discharging said output capacitor to deliver a stimulation pulse to said tissue;

means for measuring the voltage across said output capacitor; and control means, connected to said stimulation pulse generator and to said means for measuring, for enabling discharge of said output capacitor at selected times, said control means including means for setting a selected stimulation pulse amplitude, means for setting a selected minimum time interval between successive stimulation pulses, and means for increasing said minimum time if a time interval, from when the voltage across said output capacitor as measured by said means for measuring reaches said selected stimulation pulse amplitude until the time of discharge of said output capacitor, is shorter than a predetermined safety time interval selected by said control means.

2. An apparatus as claimed in claim 1 wherein said control means further includes time counter means, activated by said control means when said voltage across said output capacitor reaches said selected stimulation pulse amplitude and interrupted by said control means when said output capacitor is discharged, for comparing a counted value corresponding to said time interval with a time count corresponding to said safety time interval.

3. An apparatus as claimed in claim 1, wherein said control means further includes time counter means, enabled for counting by said control means only during said safety time interval, for generating a count beginning when said voltage across said output capacitor reaches said selected stimulation pulse amplitude, and means for detecting whether said time counter means has ceased counting before discharge of said output capacitor.

4. An apparatus as claimed in claim 1 wherein said control means further includes time counter means for generating a count beginning at the time of discharge of said output capacitor and ceasing when said voltage across said output capacitor reaches said selected stimulation pulse amplitude, means for calculating said time interval by adding said count to a count corresponding to said selected minimum time interval to obtain a calculated time interval, and means for comparing said calculated time interval with said safety time interval to establish whether said calculated time interval is shorter than said safety time interval.

5. An apparatus as claimed in claim 1 further comprising:

detector means adapted for electrical connection to said tissue to be stimulated for detecting a response from said tissue when a stimulating pulse is delivered to said tissue; and wherein said means for setting a selected stimulation pulse amplitude is connected to said detector means, and includes means for setting said selected stimulation pulse amplitude at a defined safety margin from a lowest stimulating pulse amplitude which causes a response from said tissue.

6. An apparatus as claimed in claim 1 wherein said control means further includes means for cycling said control means through a plurality of cycles with said means for increasing said minimum time interval increasing said minimum time interval in a plurality of iterative steps in the respective cycles until said time interval exceeds said safety time interval.

7. An apparatus as claimed in claim 1 wherein said means for increasing said minimum time interval increases said minimum time interval in a single step, and where said control means further includes means for making said single step long enough to make said time interval exceed said safety time interval.

8. An apparatus as claimed in claim 7, wherein said control means further includes means, after said minimum pulse time interval has been increased to a new value, for slowly decreasing said new value toward an immediately preceding value of said stimulating pulse time interval until said time interval is equal to said safety time interval.

* * * * *